(12) United States Patent
Kim

(10) Patent No.: US 9,205,118 B2
(45) Date of Patent: Dec. 8, 2015

(54) PHARMACEUTICAL COMPOSITION AND FOOD COMPOSITION FOR PREVENTING AND AMELIORATING MOTILITY DISORDERS OF GASTROINTESTINAL TRACT

(75) Inventor: Seong Jin Kim, Gwangju (KR)

(73) Assignee: ECODERM, INC., Gwangju (KR)

( * ) Notice: Subject to any disclaimer, the term of this patent is extended or adjusted under 35 U.S.C. 154(b) by 0 days.

(21) Appl. No.: 14/129,325

(22) PCT Filed: Jul. 2, 2012

(86) PCT No.: PCT/KR2012/005221
§ 371 (c)(1),
(2), (4) Date: Dec. 26, 2013

(87) PCT Pub. No.: WO2013/005956
PCT Pub. Date: Jan. 10, 2013

(65) Prior Publication Data
US 2014/0147534 A1    May 29, 2014

(30) Foreign Application Priority Data

Jul. 1, 2011  (KR) .................. 10-2011-0065685
Aug. 4, 2011  (KR) .................. 10-2011-0077932

(51) Int. Cl.
*A01N 65/00* (2009.01)
*A61K 36/14* (2006.01)
*A23L 1/30* (2006.01)

(52) U.S. Cl.
CPC .............. *A61K 36/14* (2013.01); *A23L 1/3002* (2013.01)

(58) Field of Classification Search
CPC ...................................... A61K 36/00
USPC ....................................... 424/725
See application file for complete search history.

(56) References Cited

FOREIGN PATENT DOCUMENTS

| CN | 001322482 | 11/2001 |
|---|---|---|
| CN | 001322553 | 11/2001 |
| JP | 2003-235509 | 8/2003 |
| JP | 2003235509 | * 8/2003 |
| KR | 2003-0081181 | 10/2003 |
| KR | 10-2007-0057108 | 6/2007 |
| KR | 2007-0057108 | 6/2007 |
| KR | 10-2009-0042073 | 4/2009 |
| KR | 10-2009-0075950 | 7/2009 |
| KR | 2009-0075950 | 7/2009 |
| KR | 2010-0065643 | 6/2010 |
| KR | 10-2010-0128733 | 12/2010 |
| KR | 2010-0126223 | 12/2010 |
| KR | 10-2011-0008396 | 1/2011 |
| RU | 2287303 | 11/2006 |

OTHER PUBLICATIONS

Sovilj, apteff, 41,1-203,2010.*
The Journal of Microbiology, "Inhibitory Effect of the Essential Oil from *Chamaecyparis obtusa* on the Growth of Food-Borne Pathogens," Park, Mi-Jin et al., Aug. 2010, vol. 48, pp. 496-501.
"Pharmakologische Untersuchungen über Hinokitiol (m-Isopropyltropolon)1", Archiv für Experimentelle Pathologie und Pharmakologie, 1954, vol. 221, No. 3, pp. 215-218.
Bulletin of JSSD, "Evaluation of Odors from Woods and Wood Oils," Erauchi Fumio, Aoki Hiroyuki, Ohgama Toshimasa, Kubo Mitsunori, Susuki Tsuomu, Mar. 14, 1994, pp. 11-18.

* cited by examiner

*Primary Examiner* — Michael Meller
(74) *Attorney, Agent, or Firm* — Lex IP Meister, PLLC

(57) ABSTRACT

The *Chamaecyparis obtusa* extract can be extracted by various methods. For instance, an extraction solvent may be applied to leaves, trunks or branches of the *Chamaecyparis obtuse* for hot water extraction, cold solvent immersing extraction or warm solvent immersing extraction. In this case, the extraction solvent is added to the *Chamaecyparis obtuse* 2 to 20 times in a weight ratio to then be mixed, followed by extracting at 10 to 150 for 1 to 24 hours. Here, at least one selected from the group consisting of water, C1-C4 lower alcohols, polyalcohols or mixtures thereof may be used as the extraction solvent. The C1-C4 lower alcohols may include methanol, ethanol, and so on. The polyalcohols may include butylene glycol, propylene glycol, pentylene glycol. The mixtures may include a mixture of water and a lower alcohol, a mixture of water and a polyalcohol, a mixture of water and a lower alcohol and a polyalcohol, or a mixture of water, a lower alcohol and a polyalcohol.

1 Claim, 3 Drawing Sheets

US 9,205,118 B2

PHARMACEUTICAL COMPOSITION AND FOOD COMPOSITION FOR PREVENTING AND AMELIORATING MOTILITY DISORDERS OF GASTROINTESTINAL TRACT

TECHNICAL FIELD

The present invention relates to a pharmaceutical composition and a food composition for preventing and ameliorating motility disorders of a gastrointestinal tract, and more particularly, to a pharmaceutical composition which is effective in prevention and treatment of motility disorders of the gastrointestinal tract using *Chamaecyparis obtusa* extract and a food composition which can be used as food.

Background Art

A gastrointestinal tract motility regulator may be used for functional indigestion or constipation, irritable bowel symptoms, diabetic gastrointestinal motility disorders, chemotherapeutic gastrointestinal motility disorders, intestinal obstruction due to digestive tract motility disorders, or gastrointestinal tract motility disorders of myotonic dystrophy patients.

The motility of the gastrointestinal tract is regulated by the extrinsic nervous system such as sympathetic nerves or parasympathetic nerves, the intrinsic nervous system in the gastrointerstinal tract, or intrinsic factors or drugs. In addition, autonomic factors of the gastrointerstinal tract, such as spontaneous activity of the intestinal smooth muscle and interstitial cells of Cajal (ICC), are also involved in the gastrointestinal motility.

Intensive research conducted with animal models over the past decade revealed that functions of a pacemaker in smooth muscles demonstrating typical phasic movement in the stomach, small intestine and large intestine originate in the ICC (Huizinga J D, Zarate N, Farrugia G. Physiology, Injury, and Recovery of Interstitial Cells of Cajal: Basic and Clinical Science, Gastroenterology, 2009 November; 137(5): 1548-56).

The ICC is known as a main cell for controlling the motility of the gastrointestinal tract, and physiological functions of the ICC include: 1) induction of slow waves causing spontaneous shrinkage of the smooth muscle; 2) being responsible for propagation of slow waves from a portion of the gastrointerstinal tract; 3) involving in neurotransmission between nerve endings and smooth muscles; and 4) serving as a modulator of sensory stimulus, such as a stretch receptor.

The ICC expresses a c-kit gene which is a proto-oncogene, and immunohistochemical tests are used to identify ICC in tissues. In addition, it is known that a stem cell factor (SCF) of c-kit ligand is essential for ICC development.

Presently, research into the ICC is mostly morphologically conducted. Accordingly, a reduction in the number of ICCs and a morphological change of ICC are clinically observed in intestinal obstruction, achalasia, Hirschsprung's disease, chronic constipation, and diabetic gastrointerstinal tract disorders, suggesting that movement disorders caused by diseases associated with gastrointestinal motility are closely related with the ICC (Ohlsson B, Veress B, Lindgren S, Sundkvist G. Enteric ganglioneuritis and abnormal interstitial cells of Cajal: Features of inflammatory bowel disease. Inflamm Bowel Dis. 2007 June; 13(6): 721-6/Ordog T. Interstitial cells of Cajal in diabetic gastroenteropathy. Neurogastroenterol Motil. 2008 January; 20(1): 8-18).

DISCLOSURE OF THE INVENTION

In order to overcome the above-mentioned shortcomings, the present invention provides a pharmaceutical composition and a food composition for preventing and ameliorating motility disorders of a gastrointestinal tract using *Chamaecyparis obtusa* extract. More particularly, the objective of the present invention is to confirm that the motility of the gastrointestinal tract can be regulated by changing the electrical activity of ICC.

To achieve the objectives of the present invention, there is provided a pharmaceutical composition for preventing and ameliorating motility disorders of a gastrointestinal tract, the pharmaceutical composition comprising *Chamaecyparis obtusa* extract contained as an active ingredient.

The motility disorders of the gastrointestinal tract may be prevented and ameliorated by varying the electrical activity of interstitial cells of Cajal (ICC). The *Chamaecyparis obtusa* extract may be obtained by extracting at least one of *Chamaecyparis obtusa* leaves, trunks and branches using a supercritical fluid extraction method or a hot water extraction method.

The supercritical fluid extraction method may be performed for 30 to 240 minutes by applying carbon dioxide as a supercritical fluid at a temperature of 35 to 45° C. under a pressure of 100 to 500 bar.

In addition, to achieve the objectives of the present invention, there is provided a food composition including *Chamaecyparis obtusa* extract contained as an active ingredient.

Advantageous Effect(s)

As described above, according to the present invention, diseases associated with gastrointestinal tract motility disorders, such as functional indigestion or constipation, irritable bowel symptoms, diabetic gastrointestinal motility disorders, chemotherapeutic gastrointestinal motility disorders, intestinal obstruction due to digestive tract motility disorders, or gastrointestinal tract motility disorders of myotonic dystrophy patients, can be prevented and ameliorated. More particularly, the motility of the gastrointestinal tract can be effectively regulated by changing the electrical activity of ICC.

BRIEF DESCRIPTION OF THE DRAWINGS

The objects, features and advantages of the present invention will be more apparent from the following detailed description in conjunction with the accompanying drawings, in which.

BEST MODE FOR CARRYING OUT THE INVENTION

Figure 1:
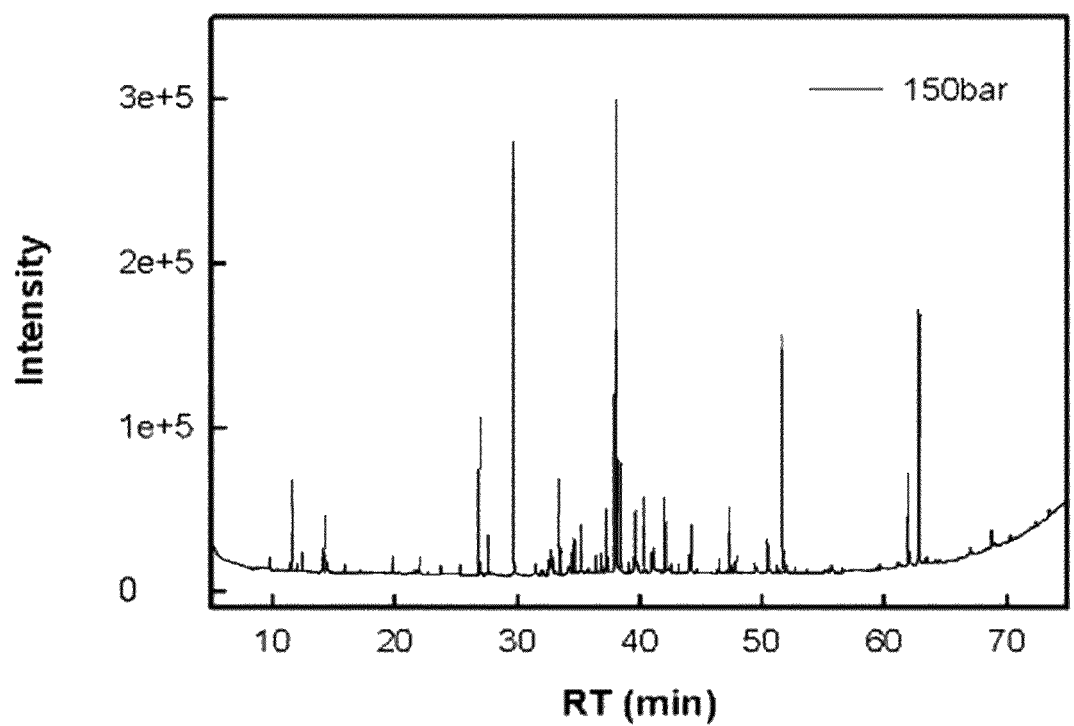
FIGS. 1 to 4 are graphs illustrating GC/MS analysis results of *Chamaecyparis obtusa* extract according to exemplified embodiments of the present invention.

Hereinafter, a pharmaceutical composition and a food composition for preventing and treating motility disorders of a gastrointestinal tract according to a preferred embodiment of the present invention will be described in detail.

The pharmaceutical composition and a food composition for preventing and treating motility disorders of a gastrointestinal tract according to a preferred embodiment of the present invention includes *Chamaecyparis obtusa* extract as an active ingredient.

The *Chamaecyparis obtusa* extract can be extracted by various methods. For instance, an extraction solvent may be applied to leaves, trunks or branches of the *Chamaecyparis*

*obtuse* for hot water extraction, cold needle or thermoneedle extraction. In this case, the extraction solvent is added to the *Chamaecyparis obtuse* 2 to 20 times in a weight ratio to then be mixed, followed by extracting at 10 to 150□ for 1 to 24 hours. Here, at least one selected from the group consisting of water, C1-C4 lower alcohols, polyalcohols or mixtures thereof may be used as the extraction solvent. The C1-C4 lower alcohols may include methanol, ethanol, and so on. The polyalcohols may include butylene glycol, propylene glycol, pentylene glycol. The mixtures may include a mixture of water and a lower alcohol, a mixture of water and a polyalcohol, a mixture of water and a lower alcohol and a polyalcohol, or a mixture of water, a lower alcohol and a polyalcohol.

In addition, the *Chamaecyparis obtusa* extract may be acquired using reflux extraction, ultrasonic extraction, or supercritical fluid extraction. In addition, the *Chamaecyparis obtusa* extract may also include extracts obtained by the extraction methods stated above and general purification. For example, the *Chamaecyparis obtusa* extract may also include active fractions obtained by an extraction method using an ultrafiltration membrane having a constant molecular weight cut-off value, a variety of chromatography based extraction methods, a variety of additionally conducted purification methods.

The *Chamaecyparis obtusa* extraction according to a preferred embodiment of the present invention is extracted from at least one of leaves, trunks and branches of *Chamaecyparis obtuse* using hot water extraction or supercritical fluid extraction.

In particular, the *Chamaecyparis obtusa* extraction is preferably extracted using the supercritical fluid extraction.

In an example embodiment of the hot water extraction, water may be added 5 to 15 folds in a weight ratio to *Chamaecyparis obtusa*, followed by extracting at 80 to 120° C. for 5 to 20 hours.

The supercritical fluid extraction exhibits high extraction efficiency because of low viscosity of a supercritical fluid used and high penetration efficiency and a high extraction speed because of a high diffusion coefficient. In addition, the supercritical fluid extraction is performed at a relatively low temperature, thereby avoiding thermal damages. Further, the supercritical fluid extraction has an advantage in that extraction residues and the solvent can be easily separated due to a big density difference between the sample and the supercritical fluid.

The supercritical fluid is a fluid maintained at a high temperature and pressure by applying critical temperature and pressure to a supercritical target material, such as carbon dioxide, water, alcohol, or helium. The supercritical fluid has substantially the same density as a liquid, a viscosity close to that of a gas and a diffusivity of approximately 100 times larger than typical liquids. The supercritical fluid is allowed to penetrate into an extraction target, thereby obtaining a high purity extract.

In the present invention, carbon dioxide may be used as the supercritical fluid, and preferred extraction conditions include 35 to 45° C., 100 to 500 bar in pressure, and 30 to 240 min in extraction time. The higher the pressure is, the higher the extraction efficiency is. In this case, however, the content of phytoncide ingredients is reduced. Therefore, the pressure for increasing the content of phytoncide ingredients having a small molecular weight is preferably in a range of 150 to 200 bar.

For preprocessing of supercritical extraction, cleaning, drying and pulverizing of *Chamaecyparis obtuse* may be performed. In order to prevent phytoncide ingredients from being volatilized from *Chamaecyparis obtuse*, the drying is preferably low temperature cold air drying or free drying.

During supercritical extraction, a mixed fluid having a cosolvent additionally mixed with carbon dioxide as the supercritical fluid may be used. The cosolvent may be at least one of ethanol, methanol, water, ethylacetate, hexane and diethylether. Specifically, 80% to 100% ethanol is preferably used as the cosolvent.

The pharmaceutical composition for regulating the motility of the gastrointestinal tract according to the present invention may comprise 0.01 to 99 wt %, preferably 0.05 to 50 wt %, of *Chamaecyparis obtusa* extract, based on the total weight of the pharmaceutical composition.

The pharmaceutical composition according to the present invention may include a formulation in the form of oral preparation such as powder, granules, tablets, capsules, suspensions, emulsions or syrups, injectable, inhalant, suppository, or patch.

The pharmaceutical composition according to the present invention may further include a pharmaceutically acceptable carrier, excipient or diluents according to desired form of formulation.

In a case of oral administration, the pharmaceutical composition according to the present invention may include, for example, a pharmaceutically acceptable excipient, such as a binder (e.g., pregelatinized corn starch, polyvinylpyrrolidone, hydroxypropyl methylcellulose, etc.); a filler (e.g., lactose, lactose, microcrystalline cellulose, calcium phosphate, etc.); lubricants (e.g., magnesium stearate, talc, silica, etc.), a disintegrating agent (e.g., potato starch, sodium starch glycolate, etc); or a wetting agent (e.g., sodium lauryl sulfatel, etc.). Representatively, the pharmaceutical composition according to the present invention may include granules, powder, tablets, capsules, which are solid dosage forms. Specifically, the tablets or the capsules may be coated by a method known in the related art.

Liquid formulations for oral administration may include, for example, syrups, emulsions or suspensions, or may exist as dry products to be combined with water or other appropriate vehicles before use.

The liquid formulations may further include pharmaceutically acceptable additives, for example, a suspension formulation (e.g., sorbitol syrup, methylcellulose, hydroxyl-propyl methylcellulose, hydrogenised edible fat, etc.); an emulsifier (e.g., lecithin, Arabian gum, etc.); a nonaqueous vehicle (e.g., almond oil, oily ester, ethyl alcohol, etc.); or an antiseptic agent (e.g., methyl or propyl p-hydroxybenzoate, sorbic acid, etc.). Preferably, pharmaceutically acceptable sweeteners may include at least one sweetener, for example, saccharin, sodium saccharin, calcium saccharin, aspartame, acesulfame potassium, sodium cyclamate, alitame, dihydrochalcone sweetener, monellin, stevioside or sucralose (4,1',6'-trichloro-4,1',6'-trideoxygallactosucrose), and an arbitrary bulk sweetener (e.g., sorbitol, manitol, fructose, sucrose, maltose, isomolt, glucose, hydrogenised glucose syrup, xylitol, caramel, honey, etc.).

A non-oral formulation includes sterilized aqueous solution, a non-aqueous solvent, a suspension, an emulsifier, a freeze drying agent, a suppository and so on. Propylene glycol, polyethylene glycol, a vegetable oil such as olive oil, injectable ester such as ethyl oleate may be used as the non-aqueous solvent and the suspension. Witepsol, macrogol, tween 61, cacao butter, laurin butter, or glycerogelatin may be used as a base of the suppository.

Desired dosages of the pharmaceutical composition according to the present invention may vary according to the status and body weight of a patient, severity of disease, drug form, dosage route and period, and so on, but may also be appropriately selected by one skilled in the art. For example, the pharmaceutical composition according to the present invention may be administered in a dose of 0.0001 to 100 mg/kg, preferably 0.001 to 100 mg/kg, per day. The dose of the pharmaceutical composition according to the present invention may be administered once a day or several times a day.

The pharmaceutical composition according to the present invention may be administered to mammals including livestock and humans in various routes. The pharmaceutical composition according to the present invention may be administered by oral, rectal, intravenous, intramuscular, subcutaneous, intravaginal, transdermal, endocranial or intracerebral injection.

In alternative embodiment, the present invention provides a food composition comprising the *Chamaecyparis obtusa* extract as an active ingredient, thereby regulating the motility of the gastrointestinal tract. The food composition according to the present invention may include the *Chamaecyparis obtusa* extract in an amount of 0.01 to 60 wt % based on a total weight of the food composition.

The food composition means food routinely taken by a human and collectively refers to something for a human to eat and drink, but the present invention does not limit the type of the food composition. The food composition may be formulated by mixing with known food supplementary or additives in various types, including beverage, granules, powder, pills, capsules, natural food, noodles, confectionary, meat, fish, herb salad, stew, boiled rice and so on. The food composition is preferably prepared as one formulation selected from drinkables, granules, powder, pills, and capsules. The formulation of the food composition is easy to carry and take at any time anywhere.

Examples of the food additive may include saccharides such as a monosaccharide, a disaccharide, a polysaccharide or a sugar alcohol, a flavoring agent such as thaumatin, a stevia extract, saccharin or aspartame, a nutrient supplement, vitamins, edible electrolyte, a flavoring agent, a coloring agent, an enhancer (e.g., cheese, chocolate, etc.), fectic acid, alginic acid, organic acid, protective colloid thickening agent, a pH regulator, a stabilizer, an antiseptive agent, glycerin, alcohol, and carbonizer.

Examples of the beverage may include 0.01 to 60 wt % of *Chamaecyparis obtusa* extract, 5 to 70 wt % of purified water, 0.1 to 5 wt % of taurin, 0.1 to 5 wt % of citric acid, 0.1 to 5 wt % of vitamin A, 0.1 to 5 wt % of vitamin B, and 10 to 20 wt % of carbohydrate. Examples of the carbohydrate may include general sugar including a monosaccharide such as glucose or fructose, a disaccharide such as maltose or sucrose, and a polysaccharide such as dextrin or cyclodextrin, xylitol, sorbitol, erythritol, and so on.

Additionally, the food composition may further include various kinds of flavoring agents together with the general beverage. Examples of the flavoring agents may include a natural flavoring agent such as thaumatin or a stevia extract, and a synthetic flavoring agent such as saccharin or aspartame. In addition, the beverage may include fruit pulp for preparing natural fruit juice or vegetable drink, which may be used alone or in combination.

The solid formulation such as granules, powder, tablets or capsules may include 0.01 to 60 wt % of *Chamaecyparis obtusa* extract and may further include additional adhesives, vitamins, and carbohydrates.

Hereinafter, the following examples are provided for a better understanding of the present invention, but the examples are simply provided as one of various embodiments and are meant to be exemplary, not exhaustive.

<Extraction Test>

1. Collecting and Pre-Processing Samples

Trees growing in the area of Jangsung, the southern part of Korea, were used in this test. The *Chamaecyparis obtuse* trees collected in October 2010 were purchased from Jangsung *Chamaecyparis Obtuse* Farming Union Corporation and used in the test.

*Chamaecyparis obtusa* leaves were isolated and washed with water to remove alien materials, contained in a polyethylene plastic bag and sealed for storage in a 4° C. cold storage room to be used as the sample. Low temperature cold air drying was employed. The low temperature cold air drying was conducted using a low temperature cold air dryer (GCT-0615, Green Cool Tech) at 35° C. for about 24 hours. The dried *Chamaecyparis obtuse* leaves were pulverized using a mixer to then be immediately extracted using a supercritical fluid extraction device.

2. Extraction Process Condition

The pre-processed *Chamaecyparis obtusa* sample (that is, pulverized *Chamaecyparis obtusa* leaves) were extracted using equipment (SCFE-0500, Il-shin Autoclave, Co., Ltd., Korea) for supercritical fluid extraction ($CO_2$ Supercritical Fluid Extraction (0.5 L)).

Before injecting the sample into a crystallization tank, the temperature of the crystallization tank was preheated to 40° C. If the temperature of the crystallization tank is stabilized at 40° C., the *Chamaecyparis obtusa* sample was injected into the crystallization tank using a high pressure pump, and a predetermined amount of an anti-solvent ($CO_2$) was injected through an upper line until the pressure of the crystallization tank reached a test pressure of 100 to 500 bar. While injecting the gas, a valve was controlled such that the pressure of the crystallization tank linearly varied. In a predetermined time (30 to 240 min) after injecting the gas, the valve installed at a lower portion of the crystallization tank is opened for slow gas exhaustion, while injecting pure $CO_2$ gas from a top upper portion of the crystallization tank, thereby maintaining the pressure of the crystallization tank at a constant level. After the pure $CO_2$ gas was injected, the pressure was reduced, yielding the *Chamaecyparis obtusa* extract.

3. Extraction Efficiency of *Chamaecyparis Obtusa* Extract

In order to investigate the extraction efficiency of the *Chamaecyparis obtusa* extract according to extraction conditions, while fixing the extraction temperature was fixed at 40° C., the time-dependent extraction yields (%) for various extraction pressures were calculated and the result is shown in Table 1. The extraction yield (%) was calculated using the formula, Extraction amount (g)/Sample dose (g)×100. The extraction amount (g) was calculated by subtracting the sample amount after extraction from the sample dose.

TABLE 1

| | | Extraction time (min) | | | | | | | |
|---|---|---|---|---|---|---|---|---|---|
| | | 30 | 60 | 90 | 120 | 150 | 180 | 210 | 240 |
| Extraction pressure (bar) | 100 | 65% | 74% | 87% | 97% | 99% | 99% | 100% | 100% |
| | 150 | 61% | 76% | 78% | 80% | 90% | 93% | 97% | 100% |
| | 200 | 68% | 80% | 85% | 90% | 92% | 93% | 96% | 100% |
| | 250 | 64% | 75% | 81% | 85% | 92% | 95% | 98% | 100% |
| | 300 | 57% | 68% | 76% | 84% | 88% | 91% | 96% | 100% |
| | 400 | 54% | 63% | 76% | 88% | 93% | 97% | 100% | 100% |
| | 500 | 55% | 68% | 74% | 81% | 88% | 95% | 98% | 100% |

Referring to Table 1, under the same pressure, the extraction efficiency increased with the lapse of time. In general, it was confirmed that in a case of hot water extraction, the extraction yield was less than 5%, and in a case of supercritical fluid extraction, the extraction yield was very high.

4. Analysis of ingredients of *Chamaecyparis Obtusa* Extract

The extracted *Chamaecyparis obtusa* extract sample was fully agitated in hexane and floating particles were removed using a centrifugal device and filtered using a microfilter (0.45 μm) to prepare the *Chamaecyparis obtusa* extract. The analysis of ingredients of *Chamaecyparis obtusa* extract was carried out using GC/MS equipment (240-MS, Varian) under the following conditions: VF-5 ms column (30 mm×0.25 mm×0.25 mm), He (1 mL/min) as a carrier gas, injection temperature of 250° C., oven temperature elevating rate of 50 to 300° C./3° C., injection volume of 1 μl, and a split ratio of 10:1 as injection mode. The ingredients were quantitatively weighed using a mass selective detector (MDS) with a mass range of 28 to 550 in a scan mode for acquisition.

First, delays of the ingredients of the *Chamaecyparis obtusa* extract were extracted under the extraction conditions of 40° C., 150 bar and 180 min, were measured and shown in the GC/MS graph of FIG. 1. The measured delays were compared with delay time of 33 kinds of standard materials of phytoncide and the qualitative analysis results of the *Chamaecyparis obtusa* extract are shown in Table 2.

TABLE 2

| Substance | RT (min) | Substance | RT (min) | Substance | RT (min) |
|---|---|---|---|---|---|
| Camphene | 10.881 | Isobornyl acetate | 18.832 | alpha-gurjunene | 32.781 |
| Sabinene | 11.988 | Thujone | 20.315 | alpha-(-)cedrene | 33.136 |
| Pinene(-)-B- | 12.204 | Terpinene-4-ol | 22.504 | Caryophyllene(-)-trans- | 33.289 |
| Myrcene | 12.913 | Terpineol-alpha | 23.229 | beta-caryophyllene | 33.29 |
| Phellandrene | 13.716 | alpha-fenchyl acetate | 24.276 | beta-chamigrene | 35.855 |
| alpha-terpinene | 14.262 | Bornyl acetate | 27.39 | Nerylisobutyrate | 36.031 |
| Cymene 4- | 14.662 | alpha-thujone | 27.502 | cis-nerolidol | 37.859 |
| Limonene | 14.851 | Longifolene | 32.857 | Nerolidol trans- | 39.065 |
| Terpinene-r | 16.385 | Longipinene | 30.279 | cis-hexanyl benzoate | 39.508 |
| Terpinolene | 17.755 | Linalyl acetate | 25.79 | Cedrol | 40.913 |
| Linalool | 18.505 | Isolongifolene | 32.158 | Eudesmol. B. | 42.661 |

Referring to FIG. 1 and Table 1, it was confirmed that primary ingredients of the *Chamaecyparis obtusa* extract were identical with phytoncide ingredients. The phytoncide ingredients contained in the *Chamaecyparis obtusa* extract mostly exhibited peaks of 40 min or less.

In addition, it was confirmed that many peaks were demonstrated even after 40 min at higher extraction pressures. This is presumably because the ingredients of the *Chamaecyparis obtusa* leaves having large molecular weights were extracted at higher pressures. Therefore, in order to increase the content of highly volatile phytoncide ingredients having relatively small molecular weight (100~300), the ingredients of the *Chamaecyparis obtusa* extract are preferably extracted at a relatively low pressure, that is, 200 bar or less.

Next, differences in the content of the *Chamaecyparis obtusa* extract ingredients were investigated according to the pre-processing drying method. Volatilization of the highly volatile phytoncide ingredients may occur in the drying, and two kinds of drying methods, that is, low temperature cold air drying and freeze drying, were used.

Figure 2:
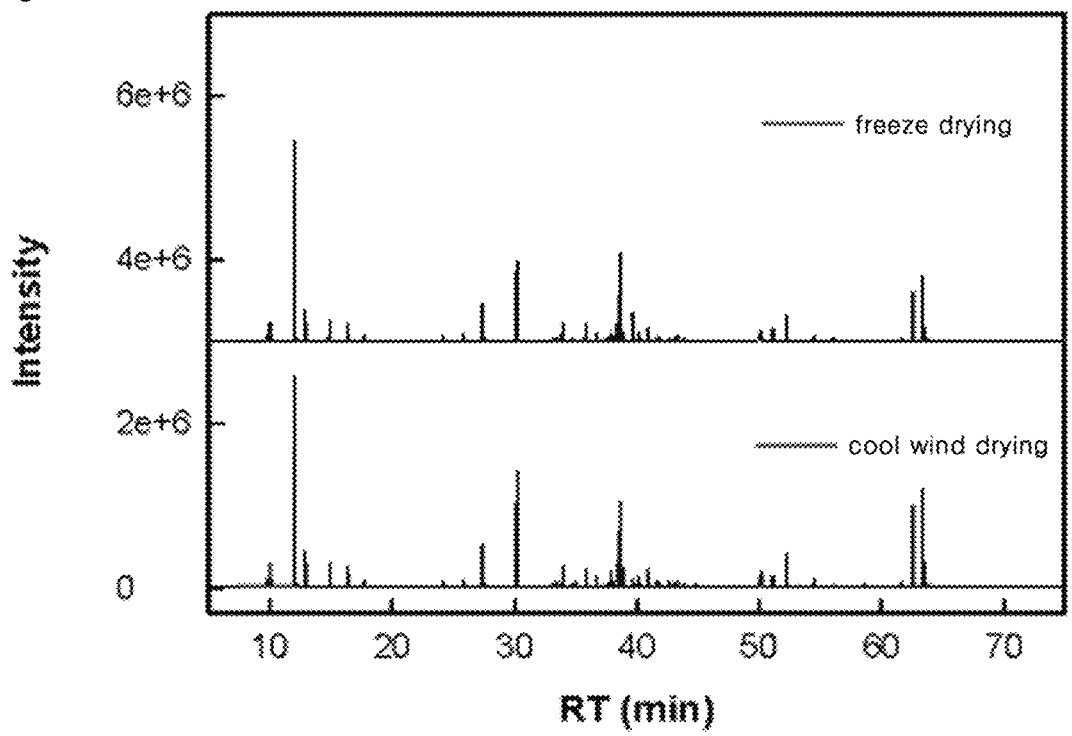

The *Chamaecyparis obtusa* extract extracted from the *Chamaecyparis obtusa* sample dried by the low temperature cold air drying (40° C., 150 bar, 180 min) and the *Chamaecyparis obtusa* extract extracted from the *Chamaecyparis obtusa* sample dried by the freeze drying (40° C., 150 bar, 180 min) were compared and shown in the GC/MS graph of FIG. 2. Table 3 shows contents of primary ingredients of *Chamaecyparis obtuse* extract. The freeze drying was conducted by drying *Chamaecyparis obtusa* leaves using a freeze dryer (OPR-FDT-8650, OPERON) for about 72 hours.

TABLE 3

| Ingredient | Content (%) during freeze drying | Content (%) during low-temperature cool wind drying |
|---|---|---|
| alpha-pinene | 0.633 | 0.676 |
| camphene | 0.092 | 0.106 |
| sabinene | 6.685 | 8.471 |
| pinene-(b) | 0.13 | 0.116 |
| myrcene | 0.957 | 1.109 |
| limonene | 1.451 | 1.608 |
| terpinene-gamma | 0.733 | 0.758 |
| terpinolene | 0.371 | 0.423 |
| alpha-fenchyl acetate | 0.37 | 0.446 |
| Linalylacetate | 0.507 | 0.679 |
| bornyl acetate | 3.038 | 3.074 |
| terpinyl acetate | 6.043 | 5.114 |

TABLE 3-continued

| Ingredient | Content (%) during freeze drying | Content (%) during low-temperature cool wind drying |
|---|---|---|
| alpha-(-)-cedrene | 0.358 | 0.323 |
| caryophyllene-trans | 0.366 | 0.423 |
| neryl isobutyrate | 1.328 | 1.552 |
| cis-nerolidol | 0.324 | 0.298 |
| Nerolidol-trans | 1.205 | 0.801 |
| Cedrol | 1.594 | 1.457 |
| Total | 26.385 | 27.434 |

Referring to FIG. 2 and Table 3, volatilization extents of the respective ingredients varied according to the drying method, but the content of the overall ingredients at the time of low temperature cold air drying was 1% higher than that at the time of freeze drying. Therefore, it was confirmed that there was no considerable difference in the content of phytoncide ingredients according to the drying method. However, the low temperature cold air drying was slightly more advantageous in view of content.

Next, in order to investigate the volatility and residual extents of phytoncide ingredients contained in the *Chamae-*

*cyparis obtusa* extract, two test samples were collected by a predetermined amount of the *Chamaecyparis obtusa* extract extracted from the *Chamaecyparis obtusa* sample dried by the low temperature cold air drying (40° C., 150 bar, 180 min), and one sample was allowed to stand undisturbed in the air and the other was sealed for storage. After 3 days, the respective samples were dissolved in hexane and then analyzed. The analysis results are shown in the GC/MS graph of FIG. 3, and contents of primary ingredients are shown in Table 4.

TABLE 4

| Ingredient | Content (%) after sealing for 3 days | Content (%) after for 3 days |
| --- | --- | --- |
| alpha-pinene | 0.62 | 0.00 |
| camphene | 0.10 | 0.00 |
| sabinene | 7.83 | 0.01 |
| pinene-(b) | 0.11 | 0.00 |
| myrcene | 1.02 | 0.00 |
| limonene | 1.49 | 0.01 |
| terpinene-gamma | 0.65 | 0.02 |
| terpinolene | 0.37 | 0.03 |
| alpha-fenchyl acetate | 0.42 | 0.29 |
| Linalylacetate | 0.65 | 0.54 |
| bornyl acetate | 2.98 | 2.65 |
| terpinyl acetate | 5.05 | 5.16 |
| alpha-(-)-cedrene | 0.32 | 0.30 |
| caryophyllene-trans | 0.41 | 0.41 |
| neryl isobutyrate | 1.52 | 1.62 |
| cis-nerolidol | 1.06 | 1.24 |
| Nerolidol-trans | 0.95 | 1.10 |
| Cedrol | 1.44 | 1.68 |
| Total | 26.98 | 15.06 |

Figure 3:
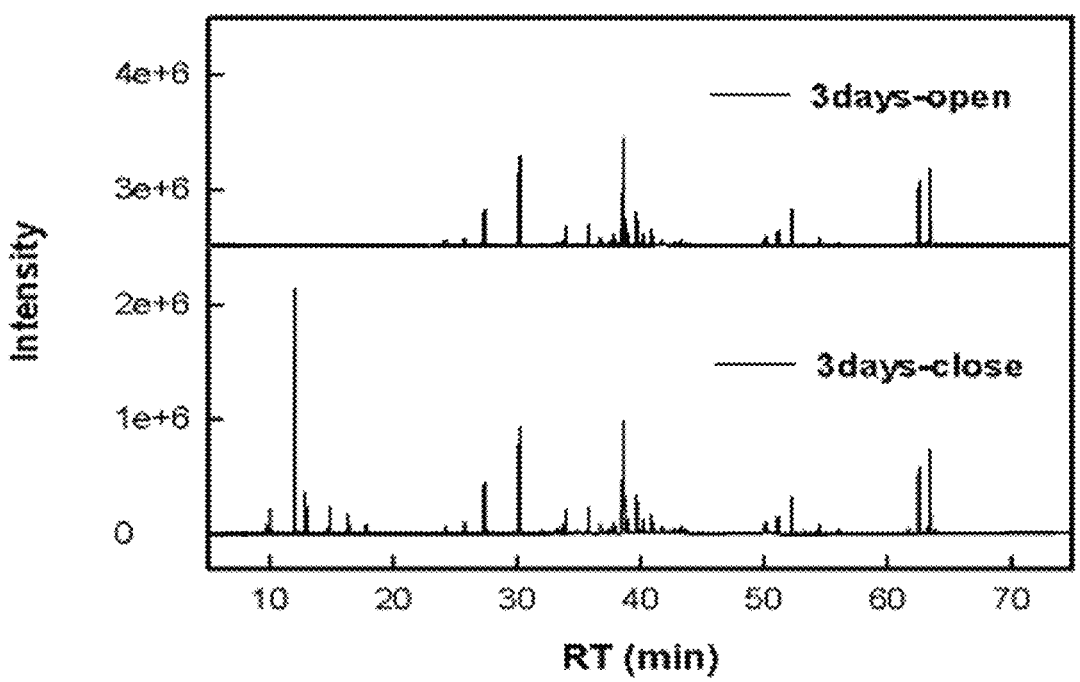

Referring to FIG. 3 and Table 4, when the *Chamaecyparis obtusa* extract was allowed to stand undisturbed in the air for 3 days, no peak was observed before 20 min. More 95% of the ingredients showing peaks before 20 min was volatilized. The ingredients showing peaks before 20 min have relatively small molecular weights and most of them were volatilized within 3 days, while the ingredients showing peaks after 40 min have relatively large molecular weight and most of them remained without being volatilized. This confirmation was definitely made at peaks before 20 min, compared to the sample sealed and stored for 3 days.

In addition, it was confirmed that some ingredients let to stand undisturbed for 3 days in the air, including cis-nerolidol, nerolidol-trans, cedrol, etc., remained in larger amounts, compared to the ingredients sealed and stored for 3 days. From this, it is presumably determined that high molecular weight ingredients were concentrated while low molecular weight ingredients were volatilized.

Through the above-described experimental results, optimum extraction conditions for obtaining large amounts of *Chamaecyparis obtusa* extracts having high content of phytoncide ingredients using supercritical fluid extraction were confirmed as being 40° C. in extraction temperature and 150 to 200 bar in extraction pressure. The appropriate extraction time is was 30 to 240 min, preferably 180 to 240 min when consideration is taken into the extraction yield.

Meanwhile, when the *Chamaecyparis obtusa* extract was extracted from the *Chamaecyparis obtusa* sample dried by the low temperature cold air drying under the conditions of 40° C., 150 bar, and 180 min among the optimum extraction conditions, changes in the ingredients depending on the number of extraction cycles were investigated. To this end, ingredients of the *Chamaecyparis obtusa* extract acquired by one cycle of extraction (1 cycle extract) and the *Chamaecyparis obtusa* extract acquired by two continuous cycles of extraction under the same condition (2 cycle extract) were analyzed. The analysis results are shown in the GC/MS graph of FIG. 4 and contents of primary ingredients are shown Table 5.

TABLE 5

| Ingredient | Content (%) of product of one extraction cycle | Content (%) of product of two extraction cycles |
| --- | --- | --- |
| alpha-pinene | 0.268 | 0.545 |
| Camphene | 0.0528 | 0.115 |
| Sabinene | 3.6192 | 6.392 |
| pinene-(b) | 0.0415 | 0.085 |
| Myrcene | 0.546 | 1.096 |
| Limonene | 1.132 | 2.057 |
| terpinene-gamma | 0.265 | 1.016 |
| Terpinolene | — | 0.469 |
| alpha-fenchyl acetate | 0.5217 | 0.926 |
| Linalylacetate | 0.524 | 1.197 |
| bornyl acetate | 3.514 | 7.632 |
| terpinyl acetate | 8.14 | 15.39 |
| alpha-(-)-cedrene | 0.295 | 0.533 |
| caryophyllene-trans | 0.441 | 1.02 |
| neryl isobutyrate | 0.849 | 2.693 |
| cis-nerolidol | 0.876 | 0.561 |
| Nerolidol-trans | 1.0326 | 2.473 |
| Cedrol | 1.485 | 1.25 |
| Total | 23.6028 | 45.45 |

Figure 4:
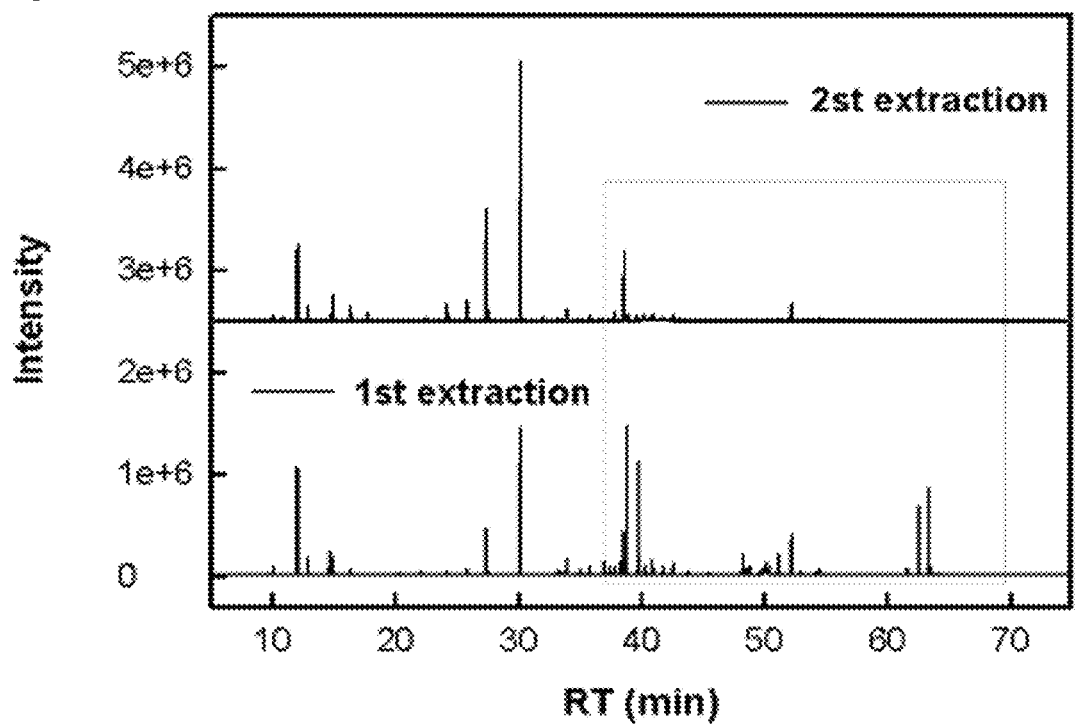

Referring to FIG. 4 and Table 5, about 23.6% of phytoncide ingredients was extracted by one cycle extraction and about 45.5% of phytoncide ingredients was extracted by two cycle extraction. Therefore, it was confirmed that high purity phytoncide ingredients could be obtained when re-extraction is made.

<Motility Regulating Test of Gastrointestinal Tract>

The motility of the gastrointestinal tract is regulated by the extrinsic nervous system such as sympathetic nerves or parasympathetic nerves, the intrinsic nervous system in the gastrointerstinal tract, or intrinsic factors or drugs. In addition, autonomic factors of the gastrointerstinal tract, such as spontaneous activity of the intestinal smooth muscle and ICC, are also involved in the motility of the gastrointestinal tract. This test is conducted to confirm that the the motility of the gastrointestinal tract can be regulated using the *Chamaecyparis obtusa* extract by varying the electrical activity of ICC.

1. Isolation of ICC 10 to 15 day aged Balb/C mice were used as test animals without distinction of male and female mice, anesthetized with ether and sacrificed by cervical dislocation. Then, the abdomen was cut open and large intestine sections were taken out. Organs were removed by cutting in a container with a Krebs-Ringer bicarbonate solution at room temperature. After the tissue was fixed with a pin, the mucosa was removed using micro dissecting scissors under optical microscope to then expose circular muscle. The isolated muscle tissue is transferred to a Hank's solution including 0.1% collagenase (Worthington Biochemical Co., Lakewood, USA), 0.1% bovine serum albumin (Sigma Chemical Co., St. Louis, Mo., USA), and 0.1% trypsin inhibitor (Sigma Chemical Co., St. Louis, Mo., USA) without $Ca^{2+}$, followed by constant temperature quenching at 37° C. for 13 minutes. Thereafter, the reaction solution was replenished by a Hank's solution without $Ca^{2+}$ and carefully shaken using a glass pipet with a blunt tip to isolate cells.

2. Cultivation of ICC

The isolated cells were divided and placed on a sterilized cover glass coated with murine collagen (2.5 g/ml, Gibco- BRL, Gaithersburg, Md., USA) in a 35 mm cultivation vessel. After 10 minutes, a smooth muscle growth medium (SmGm) (Clonetics Corp., San Diego, Calif., USA) solution containing stem cell factor (SCF) (5 ng/ml, Sigma) and 2% antibiotic/antimycotic (Gibco-BRL) was distributed, followed by cultivating in a 95% $O_2$-5% $CO_2$ cultivator at 37° C. The next day after cultivation, only 2% antibiotic/antimycotic was removed from the cultured solution to change a nutrient solution. The experiments were carried out two days after the cultivation.

The cultured ICC was identified using an antibody against kit protein (ACK2, Gibco-BRL), and immunofluorescence was performed using Alexa Fluor 488 (Molecular Probes, Eugene, Oreg., USA). After the immunofluorescence, the cells were observed using confocal laser scanning microscopy (FV300, Olympus, Japan).

3. Voltage and Current Record of Cell Membrane

The cultured media were transferred to a constant temperature controller installed on an inverted microscope and an extracellular solution was allowed to flow-through at a rate of 2 to 3 ml per minute. Whole-cell patch clamping was performed to record cell membrane voltages in a current-clamping mode and cell membrane currents in a voltage-clamping mode. Signals output from a patch clamp amplifier (Axopatch 1-D, Axon Instruments, Foster, Calif., USA) were observed by a digital oscilloscope and a physiological recording device. Adjustment of fixed and stimulating voltages and current recording were performed using a pClamp (version, 6.0, Axon Instruments) and an IBM-compatible computer. The cell membrane currents were recorded while fixing a maintenance voltage of −80 mV. The experiments were carried out at 29□.

4. Results

Figure 5:
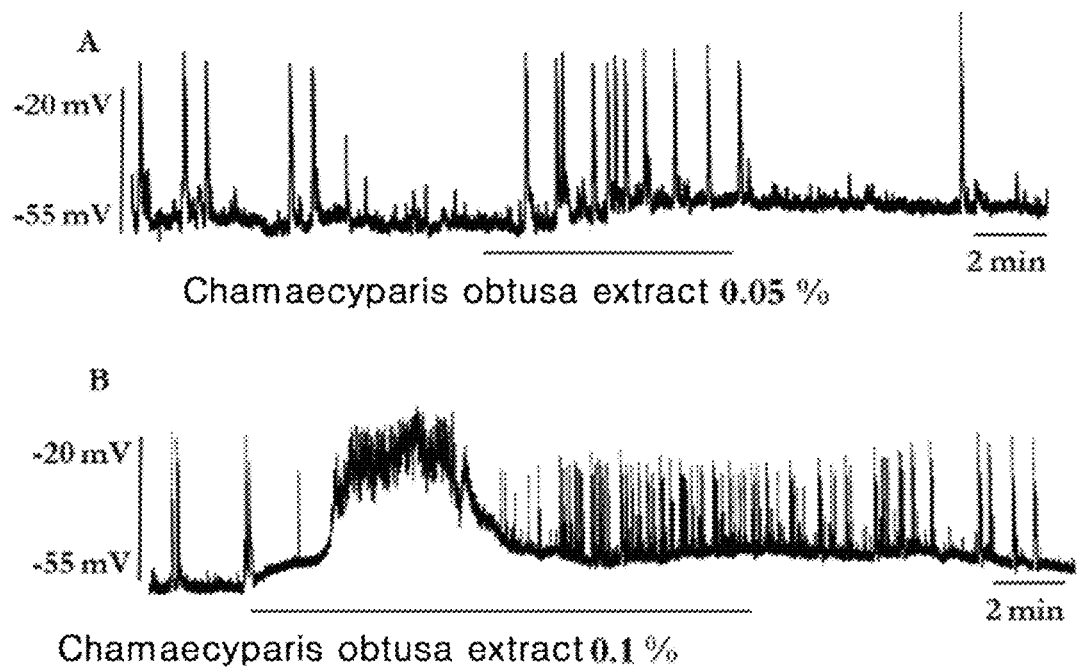
FIG. 5 is a graph illustrating a change in the electrical activity when the *Chamaecyparis obtusa* extract according to an embodiment of the present invention is treated by interstitial cells of Cajal (ICC).

In a current fixed state, the cell membrane voltage measured from ICC was −57±5 mV, and the frequency of pacemaking activity was 5±2 cycles/min. The *Chamaecyparis obtusa* extract extracted from the *Chamaecyparis obtusa* sample dried by the low temperature cold air drying (40° C., 150 bar, 180 min) was diluted with water to adjust the concentration to 0.05%. The concentration adjusted sample was administered to ICC. As confirmed from the graph (A) of FIG. 4 showing the experimental result, the frequency of occurrence of ICC pacemaker voltages increased. As confirmed from the graph (B) of FIG. 5, when 5, the concentration of the *Chamaecyparis obtusa* extract was increased to 0.1%, low polarization of the membrane voltage increased the frequency of occurrence of ICC pacemaker voltages.

As described above, the experimental results confirmed that the *Chamaecyparis obtusa* extract can regulate the the motility of the gastrointestinal tract by varying the electrical activity of ICC as pace-making cells of the gastorinterstinal tract.

Although exemplary embodiments of the present invention have been described in detail hereinabove, it should be understood that many variations and modifications of the basic inventive concept herein described, which may appear to those skilled in the art, will still fall within the spirit and scope of the exemplary embodiments of the present invention as defined by the appended claims.

INDUSTRIAL APPLICABILITY

The present invention can be efficiently used as a drug or food which is effective in preventing and treating diseases caused by motility disorders of a gastrointestinal tract, such as functional indigestion or constipation, irritable bowel symptoms, diabetic motility disorders of a gastrointestinal tract, chemotherapeutic motility disorders of a gastrointestinal tract, intestinal obstruction due to digestive tract motility disorders, or gastrointestinal tract motility disorders of myotonic dystrophy patients.

What is claimed is:

1. A tablet or capsule consisting essentially of *Chamaecyparis obtusa* extract, lactose and microcrystalline cellulose.

* * * * *